US006184003B1

(12) United States Patent
Caboche

(10) Patent No.: US 6,184,003 B1
(45) Date of Patent: Feb. 6, 2001

(54) PROCESS FOR PREPARING A CRYSTALLINE α ANHYDROUS DEXTROSE OF HIGH PURITY

(75) Inventor: Jean-Jacques Caboche, Drouvin le Marais (FR)

(73) Assignee: Roquette Freres, Lestrem (FR)

( * ) Notice: Under 35 U.S.C. 154(b), the term of this patent shall be extended for 0 days.

(21) Appl. No.: 09/328,522

(22) Filed: Jun. 9, 1999

(30) Foreign Application Priority Data

Apr. 2, 1999 (FR) .................................................. 99 04178

(51) Int. Cl.[7] ............................ C12P 19/02; C12P 19/14; C12P 19/20; C13K 1/06; C13D 3/12

(52) U.S. Cl. .............................. 435/105; 435/95; 435/99; 127/40; 127/55

(58) Field of Search .......................... 127/40, 55; 435/95, 435/99, 105

(56) References Cited

U.S. PATENT DOCUMENTS

| | | | |
|---|---|---|---|
| 3,039,935 | | 6/1962 | Rentshler et al. . |
| 3,197,338 | | 7/1965 | Hurst et al. . |
| 3,236,687 | | 2/1966 | Smith et al. . |
| 4,059,460 | | 11/1977 | Schollmeier et al. . |
| 4,422,881 | | 12/1983 | Devos et al. . |
| 4,429,122 | * | 1/1984 | Zupancic .............................. 536/124 |
| 5,869,297 | | 2/1999 | Binder et al. . |

FOREIGN PATENT DOCUMENTS 2 077 270 12/1981 (GB) .

OTHER PUBLICATIONS

Abstract in English of FR 2 762 616 (1998) *no month provided.

* cited by examiner

*Primary Examiner*—David Brunsman
(74) *Attorney, Agent, or Firm*—Henderson & Sturm LLP

(57) ABSTRACT

The invention relates to a process for preparing a crystalline α anhydrous dextrose from a starch hydrolysate, characterized in that a starch hydrolysate is prepared, said starch hydrolysate is nanofiltered over membranes in a manner such as to obtain a nanofiltration permeate constituting a syrup with a high glucose content and a nanofiltration retentate, said syrup enriched in glucose is concentrated to a dry matter content of at least 70 wt. % of glucose and at a temperature in the range 50° C. to 110° C., said concentrated syrup is crystallized by evaporation and agitation in such a manner as to obtain a crystalline mass containing at least 30 wt. % of crystals and the crystals of α anhydrous dextrose thus obtained are separated, recovered and dried.

13 Claims, No Drawings

PROCESS FOR PREPARING A CRYSTALLINE α ANHYDROUS DEXTROSE OF HIGH PURITY

FIELD OF THE INVENTION

The present invention relates to a process for preparing crystalline α anhydrous dextrose of high purity from a starch hydrolysate.

More particularly, the invention relates to a process for preparing a crystalline α anhydrous dextrose which consists in subjecting a starch hydrolysate to a nanofiltration in order to prepare a syrup with a high glucose content, then performing an evaporative crystallisation of the glucose syrup thus obtained in order to obtain crystals of α anhydrous dextrose of high purity.

BACKGROUND OF THE INVENTION

Dextrose may be produced in three crystalline forms, a hydrated form or α monohydrate form, and two anhydrous forms, i.e. the α anhydrous and β anhydrous forms.

Solid dextrose is produced classically by crystallising supersaturated syrups with a high glucose content, and the crystals obtained are crystals of α monohydrate dextrose. Moreover, this process is described in the U.S. Pat. No. 3,039,935.

As for α anhydrous dextrose itself, it is obtained classically by dissolving crystals of α monohydrate dextrose in water, then performing crystallisation at temperatures in the range 60° C. to 65° C., under carefully controlled conditions of evaporative crystallisation under vacuum.

Furthermore, there are a number of processes for manufacturing anhydrous dextrose from starch hydrolysates, for example:

the process described in the U.S. Pat. No. 3,197,338, consisting in concentrating a starch hydrolysate to a dry matter content of dextrose of at least 95% on a dry basis, preferably at least 98% on a dry basis, crystallising this by a mixing process at a temperature in the range 75° C. to 110° C., and extruding it in the form of a ribbon in a zone which cools the product to a temperature of less than 65.5° C., the process described in the U.S. Pat. No. 3,236,687, consisting in concentrating a starch hydrolysate to a dry matter content of dextrose of a value in the range 93% to 96% on a dry basis and subjecting it to a strong shear force in the presence of gas in order to form very small crystals of dextrose, the process described in the U.S. Pat. No. 4,059,460, consisting in preparing a concentrated melt of a glucose syrup with a concentration of 85% to 93% on a dry basis, at a temperature higher than 110° C. The concentrated glucose syrup is then mixed by shearing force and cooled to a temperature of less than 95° C. Finally, the glucose syrup is kept at a concentration of less then 93% and at a temperature higher than the temperature of crystallisation of α monohydrate dextrose, then shaped and converted into a solid mass. This solid mass is then granulated and dehydrated to a water content of less than 2%.

However, all these processes have two major disadvantages:

that of directly using starch hydrolysates which contain, in addition to glucose, non-negligible proportions of other sugars with a higher degree of polymerisation (DP), for example DP2 (such as maltose) and DP3 (such as maltotriose). These sugars with a higher DP result in incomplete hydrolysis, whether it be chemical or enzymatic, of said starch hydrolysate.

that of leading to mixtures of the two anhydrous forms of dextrose, at best in equivalent proportions, or even favouring the β anhydrous form, and sometimes accompanied by α monohydrate dextrose, resulting in the incorporation of residual moisture as water of crystallisation.

The crystalline dextroses obtained by these processes then have a strong tendency to agglomerate, which makes them difficult to handle. Furthermore, their flow characteristics are particularly poor.

In order to resolve the first and main disadvantage described above and to lead to the production of a dextrose with a more homogeneous crystalline structure, the patent FR 2.483.427 suggested concentrating a starch hydrolysate to a dry matter content of glucose of 92% to 99%, preferably about 95% to 99%, in a thin layer evaporator and at a temperature in the range 90° C. to 135° C.

However, the product obtained still contains more than 50% of the β anhydrous form together with the α anhydrous form, and a non-negligible proportion of amorphous structure.

The anhydrous character is obtained in this process by using particularly high temperatures, but these operating conditions also have the direct consequence of increasing the proportion of the β anhydrous form, which crystallises naturally at said temperatures.

As for the problem associated with contamination by sugars with a higher DP of the starch hydrolysates, two solutions have been suggested.

The first consists in optimising the process for preparing said starch hydrolysate.

However, although this solution reduces significantly the proportion of sugars with DP2 and DP3, it is especially difficult to obtain residual concentrations of less than 5%.

The second solution consists in using a nanofiltration process which eliminates all traces of these higher DPs, as is described in patent application FR 2.762.616, the owner of which is the assignee, or U.S. Pat. No. 5,869,297.

From all the preceding, however, it can be seen that there is an unfulfilled need to provide a crystalline α anhydrous dextrose of high purity.

In fact, all the processes of the prior art provide merely solid dextrose consisting of a mixture of the α and β anhydrous forms, or even of the monohydrate forms, associated with relatively large amounts of DP2, DP3 or even higher DPs.

OBJECTS AND SUMMARY OF THE INVENTION

Thus, the invention has the object of remedying this situation and of providing a process which responds better than existing processes to the various constraints which are met in practice.

In fact, it is obvious from the prior art that the classical processes for preparing anhydrous dextrose which require, for example, the use of two crystallisation techniques in sequence, take place in high temperature ranges which invariably lead to mixtures of the α and β crystalline forms.

The applicants have thus succeeded in refining a process producing a crystalline α anhydrous dextrose of high purity from a syrup with a high glucose content prepared by nanofiltration of a starch hydrolysate.

In the context of the invention, "crystalline α anhydrous dextrose of high purity" is understood to mean a concentration of α anhydrous dextrose of about 100 wt. %.

The process for preparing a crystalline α anhydrous dextrose according to the invention is thus characterised in that:

a) a starch hydrolysate is prepared;

b) said starch hydrolysate is nanofiltered over membranes in such a way as to obtain a nanofiltration permeate constituting a syrup with a high glucose content and a nanofiltration retentate;

c) said syrup with a high glucose content is concentrated to a dry matter content of at least 70 wt. % of glucose, at a temperature in the range 50° C. to 110° C.;

d) said concentrated syrup is crystallised by evaporation and agitation in such a manner as to obtain a crystalline mass containing at least 30 wt. % of the crystals;

e) the crystals of α anhydrous dextrose thus obtained are separated, recovered and dried.

In accordance with a first embodiment of the process according to the invention, said starch hydrolysate is a crude starch hydrolysate obtained by:

liquefaction of a starch milk using an α-amylase in such a way as to obtain a liquefied starch milk, saccharification of said liquefied starch milk using a glucogenic enzyme in such a manner as to obtain a crude saccharified hydrolysate, and optionally, microfiltration of said crude saccharified hydrolysate in such a manner as to recover a microfiltration permeate containing said crude starch hydrolysate and a microfiltration retentate.

In accordance with a second embodiment of the process according to the invention, said starch hydrolysate is a crude starch hydrolysate obtained by:

liquefaction of a starch milk using an α-amylase in such a way as to obtain a liquefied starch milk, saccharification of said liquefied starch milk using a glucogenic enzyme in such a manner as to obtain a crude saccharified starch hydrolysate with a maximum concentration of 80 wt. %, preferably a maximum concentration of 75 wt. %, and microfiltration of the crude saccharified hydrolysate in such a manner as to recover a microfiltration permeate containing said crude starch hydrolysate and a microfiltration residue.

In the context of the present invention, a "crude saccharified starch hydrolysate" is understood to mean a starch hydrolysate from which the insoluble material has been removed and which has not been subjected to any purification treatment aimed at eliminating soluble material (enzymes, proteins, amino acids, colorants, salts, etc.).

Thus, contrary to the disclosures of the prior art, which classically make provision, after saccharification, for a saccharification enzyme inhibition stage (in order to avoid the formation of reversion products), the present invention, in contrast, seeks to maintain a saccharifying enzymatic activity within the saccharified starch hydrolysate.

The present invention also seeks to maintain the presence of charges within the saccharified starch hydrolysate. In conventional processes according to the prior art, these charges are classically eliminated by passage of the saccharified starch hydrolysate over carbon black and over a demineralisation resin. In the present invention, the hydrolysate is not demineralised.

In the process according to the invention, a graded hydrolysis of the starch milk is preferably and advantageously performed in such a way as to obtain a liquefied starch milk with a low degree of conversion.

Thus, in the process according to the invention, the liquefaction stage is preferably performed up to a DE in the range 2 to 10, in particular up to a DE in the range 4 to 8.

The liquefaction stage is preferably performed in two sub-stages, the first consisting in heating the starch milk for a few minutes at a temperature in the range 105° C. to 108° C. in the presence of the enzyme (THERMAMYL 120L type, marketed by the NOVO Co.) and an activator based on calcium, the second consisting in heating the starch milk treated in this way at a temperature in the range 95° C. to 100° C. for one to two hours.

Once the liquefaction stage has been completed, under conditions relating to the dry matter content, the pH and the concentrations of enzyme and calcium which are well-known to a person skilled in the art and, advantageously, after inhibiting the liquefying enzyme (by providing, for example, a thermal shock at a temperature greater than or equal to 130° C. for a few seconds at the end of liquefaction), the liquefied starch milk is saccharified.

During this stage, the liquefied starch milk is subjected to the action of a glucogenic enzyme, in particular one chosen from the group consisting of amyloglucosidase, glucoamylase or any other glucogenic enzyme.

In order to avoid reversion reactions and the formation, in particular, of disaccharides (maltose, isomaltose) by repolymerisation of glucose, it may be advantageous to combine the glucogenic enzyme with an enzyme which specifically hydrolyses the α-1,6 bonds in starch. This disbranching enzyme is preferably isoamylase or pullulanase.

The saccharification stage is performed, under conditions and in a manner which are well-known per se, for about 12 hours to 24 hours at most in such a manner as to obtain a final hydrolysate with a concentration in the range about 50 wt. % to 95 wt. %, preferably 75 wt. % to 95 wt. %.

The amounts and conditions of action of the various enzymes used in the process according to the invention are chosen from the following:

α-amylase: 20 to 2,000 KNU (Kilo Novo Units) per kilogram of dry substrate, temperature 80° C. to 150° C., duration of action 2 minutes to 15 minutes.

amyloglucosidase: 4,000 to 400,000 international units per kilogram of dry substrate, temperature 50° C. to 60° C., duration of action 12 hours to a maximum of 24 hours, pH 4 to 6.

pullulanase: 150 to 15,000 ABM units.

The enzymes used may be of bacterial or fungal origin.

The hydrolysate saccharified in this way is then advantageously filtered, preferably by microfiltration over membranes, in such a manner as to recover a microfiltration permeate containing the crude saccharified hydrolysate and a microfiltration retentate. The conditions for this treatment, in particular with regard to temperature, are chosen in such a manner as to maintain a saccharifying enzymatic activity within the saccharified starch hydrolysate. That is why, in one preferred embodiment of the invention, the crude saccharified hydrolysate is microfiltered at a temperature which is less than or equal to the inhibition temperature of the glucogenic enzyme (the saccharification enzyme) and, advantageously, at a temperature which is substantially equivalent to the temperature of saccharification. Thus, if the temperature of saccharification is in the range 50° C. to 60° C., microfiltration should be performed at a temperature in the range 50° C. to 60° C.

The microfiltration membrane used in the process according to the invention advantageously has a porosity in the range 50 nm to 200 nm, said porosity preferably being of the order of 50 nm. The operating temperature is in the range 5° C. to 60° C. and the pressure (transmembrane pressure) is in the range 1 bar to 2 bar. A microfiltration membrane advantageously used in the process according to the invention is that marketed by the SCT Company (channels with a 4 mm diameter).

This crude saccharified hydrolysate, optionally microfiltered but not demineralised, is separated by nanofiltration over membranes in such a manner as to recover a nanofiltration permeate constituting the syrup with a high glucose content, having a concentration greater than 97%, and even more particular greater than 99%, and a nanofiltration retentate.

Contrary to all expectations, the applicants confirmed, under the same operating conditions, that better enrichment in glucose of the permeate was achieved when the saccharified hydrolysate to be nanofiltered was not demineralised. Without wishing to be tied by any particular theory, the applicants think that this better enrichment is due to the formation of a larger polarisation layer at the surface of the membrane, the formation of this supplementary filtration layer enabling the production of a higher glucose concentration in the permeate.

In accordance with a preferred embodiment, the separation over membranes is performed at temperatures in the range 30° C. to 60° C., preferably in the range 40° C. to 50° C., and at pressures in the range 15 bars to 35 bars, preferably in the range 20 bars to 30 bars. Thus the nanofiltration membrane advantageously used in the process according to the invention is of the NF40 type marketed by the FILMTEC company or of the DESAL 5 DL 3840 type marketed by the DESALINATION SYSTEMS company.

Advantageously, at least part of the nanofiltration retentate is then saccharified in such a way as to obtain a saccharified nanofiltration retentate. This secondary saccharification (with reference to the primary saccharification stage performed prior to the microfiltration stage) is possible because, during the entire process according to the invention, the necessary arrangements have been made to maintain a saccharifying enzymatic activity within the hydrolysate, in particular during the saccharification stage by not inhibiting the glucogenic enzyme at the end of the hydrolysis stage and during the microfiltration stage by working under temperature conditions similar to those in the saccharification stage.

In accordance with one variant of the process according to the invention, at least part of the nanofiltration retentate is recycled upstream of the separation stage using nanofiltration over membranes. In particular, at least part of the nanofiltration retentate is mixed with the microfiltration permeate to produce a mixture which is then advantageously saccharified. This secondary saccharification (here upstream of the separation by nanofiltration over membranes stage) is performed for a period such that the saccharified mixture has a maximum glucose concentration of 80 wt. %, preferably 75 wt. %.

If secondary saccharification is performed upstream of the nanofiltration stage, tertiary saccharification of the nanofiltration retentate is then performed in such a way as to obtain a saccharified nanofiltration retentate. The duration of this tertiary saccharification is about 48 hours.

It is then optionally possible to subject this saccharified nanofiltration retentate (obtained after performing secondary or tertiary saccharification), which may exhibit a glucose content of up to 90%, to molecular sieving in such a manner as to recover a fraction enriched in glucose and a fraction depleted in glucose.

This molecular sieving stage may consist, for example, in a chromatographic separation stage or in a separation over membranes stage.

Chromatographic fractionation is performed in a manner known per se, in a batchwise or continuous process (simulated mobile bed), on adsorbents of the cationic resin type, or on strongly acidic zeolites, preferentially charged using alkaline or alkaline earth ions such as calcium or magnesium, but in particular using sodium ions.

In accordance with a preferred embodiment, chromatographic fractionation is performed by using the process and equipment described in American U.S. Pat. No. 4,422,881, of which the Assignee is the owner. Whatever the chromatographic process used, the absorbent which is preferably employed is a strongly cationic resin, in the sodium or potassium form and cross-linked with about 4% to 10% of divinylbenzene. The resins advantageously have a homogeneous granulometry which is between 100 micrometers and 800 micrometers.

Instead of the chromatographic separation stage, it is possible, in the process according to the invention, to use a separation stage using nanofiltration over membranes of the type described above.

The fraction enriched in glucose obtained after the chromatographic stage may then be mixed with the syrup with a high concentration of glucose obtained previously.

The subsequent stages of the process according to the invention then consist in evaporative crystallisation of the syrup with a high glucose content thus obtained in order to obtain a crystalline α anhydrous dextrose of high purity.

The third stage (c) of the process according to the invention thus consists in concentrating the syrup with a high concentration of glucose to a dry matter content of at least 70 wt. %.

This concentration stage is performed in a manner known per se, for example by evaporation of the water under vacuum at a temperature of about 70° C.

The conditions relating to temperature and dry matter content are thus specifically fixed in order to locate the glucose syrup within the crystallisation zone of the α anhydrous form.

In fact, a person skilled in the art knows that, for a solution having a high glucose content, the α anhydrous dextrose crystallises in the temperature range 50° C. to 110° C., for a dry matter content greater than 70%.

In the process according to the invention, the concentration of the syrup enriched in glucose may reach a value of the order of 80% of dry matter. In such cases, a temperature of about 70° C. is preferably used.

In a first preferential embodiment according to the invention, crystallisation is initiated by adding α anhydrous dextrose to the concentrated glucose syrup, with stirring.

In a second embodiment of the process according to the invention, spontaneous nucleation is performed by any method known per se by a person skilled in the art, for example by applying a shear force to said concentrated solution.

The fourth stage (d) of the process according to the invention consists in continuing the crystallisation process by evaporation and agitation of said concentrated syrup in such a manner as to obtain a crystalline mass containing at least 30 wt. % of crystals.

The residence time in the evaporative crystallisation apparatus is of the order of 5 h to 8 h, preferably 6 h, at a temperature of about 70° C.

In a preferential embodiment according to the invention, evaporative crystallisation is performed in a rotary evaporator under a relatively high vacuum, about 50 mm Hg.

At the end of the evaporative crystallisation stage, the last stage of the process according to the invention consists in separating, recovering and drying the crystals of α anhydrous dextrose thus obtained.

The crystalline mass containing at least 30% of individual crystals is then separated from the mother liquor by any method known per se, for example by centrifuging or filtering the crystallised syrup of α anhydrous dextrose.

Preferably, the crystals are then purified by washing with water, then dried at a temperature below the melting point of α anhydrous dextrose, preferably at a temperature of about 60° C., also using any method known per se, for example in a drying cabinet or in a fluidised bed.

Use of the process according to the invention enables the production of crystals with a content of about 100% of the α anhydrous form.

More Detailed Description

Other features and advantages of the invention will appear on reading the non-restrictive example described below.

EXAMPLE 1

A starch milk is liquefied in a classical manner using 0.5 part per thousand of THERMAMYL 120L (α-amylase marketed by the NOVO Co.) up to a DE of 6.5.

The reaction mixture is then heated at 140° C. for a few seconds in such a manner as to inhibit the a-amylase.

The hydrolysate at a concentration of 35% on a dry weight basis is then saccharified in a manner known per se in the presence of 0.8 part per thousand of amyloglucosidase G990 marketed by the ABM Co. (temperature 60° C., pH=4.5).

After 24 hours of saccharification, a hydrolysate with the following glucidic range is obtained:

glucose: 93%

DP2: 2.5%

DP3: 0.5% higher DPs: 4% it being understood that the abbreviation "DP" means degree of polymerisation.

The enzymatic activity measured is 3 U/l.

The hydrolysate saccharified in this way is then filtered by microfiltration over membranes.

The operating conditions are as follows:

SCT membrane: 50 nm temperature: 60° C.

pressure: 2 bar

The enzymatic activity measured is 2.5 U/l.

The hydrolysate microfiltered in this way is divided into two to produce a hydrolysate A and a hydrolysate B.

Hydrolysate A is not demineralised. Hydrolysate B for its part is demineralised by passage over carbon black and resin.

Each of these hydrolysates A and B is subjected to nanofiltration under the following operating conditions:

DESAL 5 DL membrane temperature: 45° C.

pressure: 25 bars

The characteristics of the permeates and retentates after nanofiltration A and B of hydrolysates A and B are as follows:

| | glucose/purity | enzymatic activity |
|---|---|---|
| Permeate A | 99.7% | 0 U/l |
| Retentate A | 80% | 7 U/l |
| Permeate B | 98.5% | 0 U/l |
| Retentate B | 80% | 0 U/l |

EXAMPLE 2

Liquefaction and saccharification of a starch milk are performed in the same way as described in example 1.

After 12 hours of saccharification, a hydrolysate with the following glucidic range is obtained:

glucose: 75.8%

DP2: 2.1%

DP3 and higher: 20.1%

The enzymatic activity measured is 3 U/l.

The hydrolysate saccharified in this way is then filtered by microfiltration over membranes, under the same conditions as in example 1.

The enzymatic activity measured is 2.5 U/l.

The hydrolysate nanofiltered in this way is then divided into two to produce a hydrolysate C and a hydrolysate D.

Hydrolysate C is not demineralised. Hydrolysate D for its part is demineralised by passage over carbon black and resin.

Each of the hydrolysates C and D is subjected to nanofiltration under the following operating conditions:

DESAL 5 DL membrane temperature: 45° C.

pressure: 25 bars

The characteristics of the permeates and retentates after nanofiltration C and D of hydrolysates C and D were as follows:

| | glucose/purity | enzymatic activity |
|---|---|---|
| Permeate C | 99.4% | 0 U/l |
| Retentate C | 50% | 7 U/l |
| Permeate D | 97.9% | 0 U/l |
| Retentate D | 50% | 0 U/l |

EXAMPLE 3

Permeate A from example 1 (99.4% pure glucose) is concentrated to a dry matter content of 80% by evaporation at 70° C. and placed in a laboratory rotary evaporator with an effective volume of 2 l marketed by the BÜCHI Co.

The temperature is held at 70° C. and crystallisation is initiated by adding 5 g of α anhydrous dextrose.

Evaporative crystallisation is continued for 6 h, by continuously supplying the concentrated glucose syrup with a 80% dry material content at a rate of 1 l/h.

At the end of evaporative crystallisation, 3 kg of a crystalline material containing 50.8 wt. % of individual crystals are obtained.

The crystals are then separated from the mother liquor by centrifuging at 1000 g for 10 min using a laboratory centrifuge marketed by the ROUSSELET Co.

During this centrifuging stage, the crystals are washed with 200 ml of demineralised water.

The crystals are then dried for 15 min in a fluidised bed dryer at 60° C.

The yield of crystallisation is 56 wt. %, expressed as weight of α anhydrous dextrose to total weight of dry matter.

The purity of the crystals recovered is 99.7% on a dry basis. The water content is 0.2%.

What is claimed is:

1. A process for preparing a crystalline α-anhydrous dextrose wherein:

a) a starch hydrolysate is prepared;

b) said starch hydrolysate is nanofiltered over membranes in such a way as to obtain a nanofiltration permeate constituting a syrup with a high glucose content and a nanofiltration retentate;

c) said syrup with a high glucose content is concentrated to a dry matter content of at least 70 wt. % of glucose, at a temperature in the range 50° C. to 110° C.;

d) said concentrated syrup is crystallised by evaporation and agitation in such a manner as to obtain a crystalline mass containing at least 30 wt. % of the crystals;

e) the crystals of α anhydrous dextrose thus obtained are separated, recovered and dried.

2. A process according to claim 1, wherein said starch hydrolysate is a crude starch hydrolysate obtained by:

liquefaction of a starch milk using an α-amylase in such a way as to obtain a liquefied starch milk, saccharification of said liquefied starch milk using a glucogenic enzyme in such a manner as to obtain a crude saccharified hydrolysate, and optionally, microfiltration of said crude saccharified hydrolysate in such a manner as to recover a microfiltration permeate containing said crude starch hydrolysate and a microfiltration retentate.

3. A process according to claim 2, wherein microfiltration of the saccharified crude starch hydrolysate is performed at a temperature less than or equal to the inhibition temperature of the glucogenic enzyme.

4. A process according to claim 3, wherein at least part of the nanofiltration retentate is mixed with the microfiltration permeate in order to form a mixture and that said mixture is saccharified.

5. A process according to claim 1, wherein said starch hydrolysate is a crude starch hydrolysate obtained by:

liquefaction of a starch milk using an a-amylase in such a way as to obtain a liquefied starch milk, saccharification of said liquefied starch milk using a glucogenic enzyme in such a manner as to obtain a crude saccharified starch hydrolysate with a maximum concentration of 80 wt. %, and microfiltration of the crude saccharified hydrolysate in such a manner as to recover a microfiltration permeate containing said crude starch hydrolysate and a microfiltration retentate.

6. A process according to claim 5, wherein said crude saccharified starch hydrolysate has a maximum concentration of 75 wt. %.

7. A process according to claim 5, wherein microfiltration of the saccharified crude starch hydrolysate is performed at a temperature less than or equal to the inhibition temperature of the glucogenic enzyme.

8. A process according to claim 5, wherein at least part of the nanofiltration retentate is mixed with the microfiltration permeate in order to form a mixture and that said mixture is saccharified.

9. A process according to claim 1, wherein at least part of the nanofiltration retentate is saccharified in such a way as to obtain a saccharified nanofiltration retentate;

said saccharified nanofiltration retentate is subjected to molecular sieving in such a manner as to obtain a fraction enriched in glucose, and said fraction enriched in glucose is mixed with said syrup containing a high concentration of glucose.

10. A process according to claim 1, wherein the syrup with a high glucose content has a glucose concentration greater than 97%.

11. A process according to claim 10, wherein the syrup with a high glucose content has a glucose concentration greater than 99%.

12. A process according to claim 1, wherein the stage in which the syrup with a high glucose content is concentrated is performed by evaporation at a temperature of about 70° C.

13. A process according to claim 1, wherein the α anhydrous dextrose crystals obtained after the stage in which the syrup with a high concentration of glucose is crystallised are collected by centrifuging and dried at a temperature of about 60° C.

* * * * *